US011633316B2

(12) United States Patent
Siccardi et al.

(10) Patent No.: US 11,633,316 B2
(45) Date of Patent: Apr. 25, 2023

(54) ADAPTER PLANE FOR SURGICAL TABLE AND SURGICAL TABLE

(71) Applicant: MEDACTA INTERNATIONAL SA, Castel San Pietro (CH)

(72) Inventors: Francesco Siccardi, Castel San Pietro (CH); Massimiliano Bernardoni, Castel San Pietro (CH); Mirko Giardiello, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 844 days.

(21) Appl. No.: 16/095,166

(22) PCT Filed: Jan. 31, 2017

(86) PCT No.: PCT/IB2017/050501
§ 371 (c)(1),
(2) Date: Oct. 19, 2018

(87) PCT Pub. No.: WO2017/182889
PCT Pub. Date: Oct. 26, 2017

(65) Prior Publication Data
US 2019/0151179 A1 May 23, 2019

(30) Foreign Application Priority Data

Apr. 21, 2016 (IT) .................. 102016000041033

(51) Int. Cl.
*A61G 13/00* (2006.01)
*A61G 13/10* (2006.01)
(Continued)

(52) U.S. Cl.
CPC .......... *A61G 13/0081* (2016.11); *A61B 90/50* (2016.02); *A61G 7/0755* (2013.01);
(Continued)

(58) Field of Classification Search
CPC ............ A61G 13/0081; A61G 13/0036; A61G 13/0063; A61G 13/10; A61G 13/101;
(Continued)

(56) References Cited

U.S. PATENT DOCUMENTS 824,612 A * 6/1906 Bartlett .............. A61G 13/0036
602/39
4,624,245 A 11/1986 Mullin et al.
(Continued)

FOREIGN PATENT DOCUMENTS

DE 102005023477 A1 11/2006
DE 102010020530 A1 11/2011
(Continued)

OTHER PUBLICATIONS

English Translation of Notice of Reasons for Refusal issued on JP 2018-555148 dated Sep. 9, 2019.
(Continued)

*Primary Examiner* — Robert G Santos
(74) *Attorney, Agent, or Firm* — Meunier Carlin & Curfman LLC

(57) ABSTRACT

An adapter plane for a surgical table comprising a central body having a proximal portion suitable to at least partially accommodate the lumbar region of the body of a patient and a distal portion suitable to at least partially accommodate the sacral region of the body of a patient, wherein the adapter plane can be coupled to a surgical table by placing the central body at least partially on top of the surgical table, and the central body, in the distal portion, is provided with a quick coupling device for coupling the adapter plane to one or more surgical instruments.

17 Claims, 2 Drawing Sheets

(51) Int. Cl.
*A61G 13/12* (2006.01)
*A61G 7/075* (2006.01)
*A61B 90/50* (2016.01)
*A61B 90/57* (2016.01)

(52) U.S. Cl.
CPC ......... *A61G 13/101* (2013.01); *A61G 13/123* (2013.01); *A61G 13/1225* (2013.01); *A61G 13/1285* (2013.01); *A61G 13/1295* (2013.01); *A61B 2090/571* (2016.02); *A61G 7/075* (2013.01); *A61G 13/0036* (2013.01); *A61G 13/0063* (2016.11); *A61G 13/10* (2013.01); *A61G 2210/10* (2013.01); *A61G 2210/50* (2013.01)

(58) Field of Classification Search
CPC ................ A61G 13/12; A61G 13/1205; A61G 13/1225; A61G 13/123; A61G 13/1245; A61G 13/125; A61G 13/1285; A61G 13/1295; A61G 7/05; A61G 7/075; A61G 7/0755
USPC ..... 5/630, 621, 624, 648, 658, 600; 128/845
See application file for complete search history.

(56) References Cited

U.S. PATENT DOCUMENTS

| | | | | |
|---|---|---|---|---|
| 6,968,585 | B2* | 11/2005 | Shaw | A47C 20/021 5/648 |
| 8,584,280 | B2* | 11/2013 | Shah | A61G 13/121 5/603 |
| 8,683,631 | B2* | 4/2014 | Bellows | A61G 13/1245 5/624 |
| 8,763,177 | B2* | 7/2014 | Shah | A61G 13/123 5/603 |
| 8,997,284 | B2 | 4/2015 | Kreuzer et al. | |
| 8,997,286 | B2* | 4/2015 | Wyslucha | A61G 13/0036 5/658 |
| 8,997,749 | B2* | 4/2015 | Drake | A61F 5/04 128/845 |
| 9,233,043 | B2* | 1/2016 | Labedz | A61G 13/0036 |
| 9,597,247 | B2* | 3/2017 | Shah | A61G 13/123 |
| 9,877,886 | B2* | 1/2018 | Bernardoni | A61G 13/0036 |
| 10,149,792 | B2* | 12/2018 | Drake | A61G 13/0036 |
| 10,206,842 | B2* | 2/2019 | Labedz | A61G 13/125 |
| 10,485,720 | B2* | 11/2019 | Bernardoni | A61G 13/1225 |
| 11,077,006 | B2* | 8/2021 | Labedz | A61G 13/0081 |
| 2004/0133983 | A1* | 7/2004 | Newkirk | A61G 13/0036 5/624 |
| 2005/0060808 | A1* | 3/2005 | Shaw | A47C 20/021 5/649 |
| 2010/0122414 | A1* | 5/2010 | Shah | A61G 13/121 5/603 |
| 2011/0099720 | A1* | 5/2011 | Wyslucha | A61G 13/0036 5/658 |
| 2013/0074264 | A1* | 3/2013 | Shah | A61G 13/1225 5/603 |
| 2013/0081635 | A1* | 4/2013 | Drake | A61G 13/0036 128/845 |
| 2013/0191994 | A1* | 8/2013 | Bellows | A61G 13/1245 5/624 |
| 2013/0191995 | A1* | 8/2013 | Bellows | A61G 13/0081 5/624 |
| 2013/0192609 | A1* | 8/2013 | Bellows | A61G 13/123 128/845 |
| 2014/0215718 | A1 | 8/2014 | Wootton | |
| 2014/0263889 | A1 | 9/2014 | Hensler | |
| 2014/0289963 | A1* | 10/2014 | Shah | A61G 13/122 5/603 |
| 2015/0164724 | A1* | 6/2015 | Drake | A61G 13/0036 128/845 |
| 2015/0164728 | A1 | 6/2015 | Kreuzer et al. | |
| 2015/0196447 | A1 | 7/2015 | Henderson et al. | |
| 2015/0231013 | A1* | 8/2015 | Bernardoni | A61G 13/0036 128/845 |
| 2015/0245971 | A1* | 9/2015 | Bernardoni | A61G 13/02 5/601 |
| 2016/0158082 | A1* | 6/2016 | Gainor | A61G 7/075 5/690 |
| 2019/0117489 | A1* | 4/2019 | Labedz | A61G 13/0036 |
| 2019/0151179 | A1* | 5/2019 | Siccardi | A61G 13/1225 |
| 2020/0360100 | A1* | 11/2020 | Mantri | A61B 90/37 |

FOREIGN PATENT DOCUMENTS

| | | |
|---|---|---|
| DE | 102009047869 B4 | 5/2014 |
| DE | 202016101587 U1 | 6/2016 |
| DE | 202016101587 U1 | 8/2016 |
| EP | 0296872 A2 | 12/1988 |
| FR | 2871050 A1 | 12/2005 |
| GB | 881157 | 11/1961 |
| JP | 10277054 A | 10/1998 |
| JP | 2002543865 A | 12/2002 |
| JP | 2005168881 A | 6/2005 |
| JP | 2009504262 A | 2/2009 |
| JP | 2015533097 A | 11/2015 |
| JP | 2016524476 A | 8/2016 |
| WO | 2014045194 A1 | 3/2014 |

OTHER PUBLICATIONS

International Search Report and Written Opinion issued by the European Patent Office in application No. PCT/IB2017/050501, dated May 22, 2017. 8 pages.
Notice of Opposition received in connection with European Application No. 17711318.0 dated Jan. 22, 2021 (39 pages).
Watson, Charles, et al., "The Vertebral Column and Spiral Meninges," The Spinal Cord, published by Academic Press (an imprint of Elsevier Ltd.), pp. 17-23, 2009 (10 pages).
Letter to Innovative Orthopedic Technologies IOT AG, dated May 15, 2020, from Stefano Codoni, counsel for Medacta International SA (5 pages).
Anonymous, excerpt from Wikipedia "surgical instrument" dated Feb. 23, 2016, retrieved from https://en.wikipedia.org.wiki/Surgical_instrument, XP055782710 (1 page).
Condor GmbH Medicaltechnik, RotexTable brochure, dated Oct. 2015 (5 pages).
Condor GmbH, RotexTable manual, dated Nov. 8, 2012 (44 pages).
Transcript with screen shots of FLOTE video, which was posted to https://www.youtube.com/watch?v=gtUE1kHDwy0 as of Oct. 13, 2013 (8 pages).
Parcells, Bertrand W., et al., "The Direct Anterior Approach for 1-Stage Bilateral Total Hip Arthroplasty Early Outcome Analysis of a Single Surgeon Case Series," The Journal of Arthroplasty, vol. 31, No. 2, pp. 434-437, e-published Aug. 29, 2015 (4 pages).
Koli, Emmanuel, et al., "Simultaneous Versus Staged Total Hip Arthroplasty: A Review" (Abstract only), Bulletin of the NYU Hospital of Joint Diseases, vol. 73, No. 2, pp. 78-82, published Jun. 2015 (1 page).
Summons to attend oral proceedings pursuant to Rule 115(1) EPC received in connection with European Application No. 17711318.0 dated Oct. 12, 2021, 14 pages.
Opposition against European Patent No. 3445305 (Application No. 17711318.0), dated Sep. 2, 2021, 27 pages.
Reply to the Notice of Opposition against European Patent No. 3445305 dated Jun. 15, 2021, 24 pages.
Opposition against European Patent No. 3445305 (Application No. 17711318.0), dated Dec. 15, 2021 and mailed to patent owner on Dec. 20, 2021, 8 pages.
Opposition against European Patent No. 3445305 (Application No. 17711318.0), dated Jan. 27, 2022 and mailed to the patent owner on Feb. 2, 2022, 4 pages.
Notice of Opposition received in connection with European Patent No. 3445305 (Application No. 17711318.0), dated Dec. 30, 2020, 37 pages.

(56) References Cited

OTHER PUBLICATIONS

Mehar, Zaheer Khan, "Surgical Instrument and Sterilization Guidebook; A manual of Surgical Instruments which are primarily used in Operation Theaters and Standard protocol for sterilization", LAP LAMBERT Academic Publishing GmbH & Co. KG, published 2011, 5 pages.
https://www.collinsdictionary.com/us/word-lists/medicine-medical-and-surgical-instruments-and-equipment, "Word list: Medical and surgical instruments and equipment", 5 pages, accessed May 23, 2022 noting a copyright date of 2016.
Interlocutory Decision in Opposition for EP Patent No. 3445305, dated Nov. 17, 2022, 2 pages.
Grounds for Decision—Annex in Opposition for EP Patent No. 3445305, dated Nov. 17, 2022, 13 pages.
Druckexemplar in Opposition Proceedings in Opposition for EP Patent No. 3445305, dated Nov. 17, 2022, 10 pages.
Decision of Opposition Division and Instruction in Opposition for EP Patent No. 3445305, dated Nov. 17, 2022, 1 page.
Transmittal of Decision—Summons—Opposition in Opposition for EP Patent No. 3445305, dated Nov. 17, 2022, 80 pages.
Information about Oral Proceedings in Opposition for EP Patent No. 3445305, dated May 18, 2022, 21 pages.
Brief Communication Opposition Proceedings in Opposition for EP Patent No. 3445305, dated Mar. 24, 2022, 36 pages.

\* cited by examiner

ADAPTER PLANE FOR SURGICAL TABLE AND SURGICAL TABLE

The present invention applies to the field of orthopaedic surgery and refers, in particular, to an adapter plane for a surgical table.

Said adapter plane can usefully be applied in hip replacement operations, in particular when the anterior approach is used.

The invention also refers to a surgical table equipped with said adapter plane.

Every year a large number of patients undergo hip replacement surgery in order to restore functioning of the joint damaged by conditions such as, for example, osteoarthritis.

Operations of this type, as well as other orthopaedic surgical operations, have benefited from rapid advancements in orthopaedic techniques, such as minimally invasive surgical techniques and improvements in radiology techniques. Such radiology techniques not only enable precise preoperative planning of surgery, but have also made it possible to develop minimally invasive surgical procedures which have significantly reduced patient recovery times.

New surgical techniques have gone hand in hand with the introduction on the market of new medical devices to aid surgeons performing operations on patients. An example of such new surgical devices is the adapter plane for surgical table, in particular for hip replacement surgery with anterior approach, which is the subject of Italian patent application number MI2012A001546 filed by this same Applicant.

Said document discloses an adapter plane for surgical table, made at least partly of radiotransparent material, designed to be coupled to a conventional surgical table.

Said adapter plane is able to support a portion of the body of the patient undergoing surgery and can be coupled on one side, as already mentioned, to a conventional surgical table, and on the other to an apparatus for positioning the limb. An example of an apparatus for positioning the limb is disclosed in document FR2871050 filed by this same Applicant.

The function of the adapter plane disclosed in the prior art document is not merely to couple the surgical table to the apparatus for positioning the patient's limb, but also to support part of the patient's body.

The patient lies in a supine position on the surgical table and a substantial part of his or her body, in particular from the lumbar region to the pelvis, is supported by the adapter plane, whereas the limb on which the operation is to be performed is supported by the limb positioning apparatus.

The adapter plane disclosed in MI2012A001546 is intended for use in minimally invasive hip replacement surgery using the anterior approach.

On the side of the hip to be operated on, the prior art adapter plane is provided with a support for the patient's thigh, said support being appropriately distally spaced from the main portion of the adapter plane with respect to the surgical table. Said support acts as a support for the proximal part of the leg and, during maneuvering of the patient's limb by the surgeon, in particular during hyperextension of the leg, it acts as a fulcrum, enabling the surgeon to expose more of the proximal part of the thigh bone.

The thigh rest, as known in the prior art, has an elongated shape and projects with respect to the central axis of the adapter plane, it is spaced from the support portion, hinged to the frame of the adapter plane and can be adjusted in height using appropriate adjustment means.

This configuration clearly prevents the use of the adapter plane regardless of the leg to be operated on. Depending on whether surgery is to be performed on the right leg or the left leg, the adapter plane must be provided with a thigh rest on the right or left side, according to the leg that requires hip replacement surgery.

If the adapter plane does not have a thigh rest on the side to be operated on, it will have to be replaced with an adapter plane with a thigh rest on the correct side.

In order to make the adapter plane more versatile, a thigh rest that can be detachably coupled to the adapter plane has been developed. This arrangement means that the adapter plane with the thigh rest on the wrong side does not have to be detached from the surgical table to be replaced with an adapter plane with a thigh rest on the correct side. However, such operations take time during which the adapter plane cannot be used, and this solution requires the availability of a second adapter plane that has already been configured correctly for the operation and does not actually overcome the problem identified in the prior art. The operation of uncoupling the thigh rest and re-coupling it to the correct side could of course be performed directly in the operating theatre between a first and a second surgical operation. However, this would entail the contamination of the support by the non-sterile mechanical means used for uncoupling and subsequently re-coupling (for example, screw drivers), so that the thigh rest, at least, would require subsequent sterilisation, with the associated costs and time involved.

Therefore, to overcome this problem an adapter plane has been described with a thigh support that can be moved from one side of the adapter plane to the other, so that it can be used as a support whether the operation is performed on the left leg or on the right leg without requiring any mechanical uncoupling operations.

Unfortunately, such adapter plane is difficult to handle owing to the structural dimensions of the necessary mechanical structures that are essential in order to move the thigh rest from one side of the adapter plane to the other. Moreover, in order to place the thigh rest in the appropriate position for the operation, the adapter plane must be uncoupled from the limb positioning apparatus, the thigh rest must be moved to the correct position and the limb positioning apparatus must be re-coupled in the correct position.

From the above, it is immediately apparent that the technical problem identified in the prior art of having to use mechanical means to uncouple mechanical parts has not been solved and indeed continues to exist with the limb positioning apparatus. In fact, when the thigh rest has been moved to the correct side, the limb positioning apparatus must be uncoupled and then re-coupled on the correct side.

Moreover, this solution which already fails to overcome the known technical problem, is not suitable in the case of bilateral hip replacement surgery. This is not only because there is no second thigh rest, but also because a second limb positioning apparatus cannot be coupled to it, since there is no way of providing second coupling means thereof to the adapter plane. If second coupling means were provided for an additional limb positioning device, they would be a hindrance when maneuvering the thigh rest, making such operations very difficult, and could undermine the patient's safety.

A further inconvenience that has never been overcome by the prior art solutions regards the positioning of the surgical instruments used by the surgeon. Since these must be accessible above the drape covering the patient but are only supported and coupled beneath said drape, they require complex support structures defined by cumbersome curved arms and laborious couplings.

The aim of the present invention is to overcome the technical problems associated with the solutions known in the prior art and provide an adapter plane for surgical table, in particular for hip replacement surgery using the anterior approach, in which surgical instruments can easily be set in position and replaced.

Moreover, a further purpose of the present invention is to provide an adapter plane for surgical table that can be used in unilateral or bilateral hip replacement operations without any need to reposition the thigh rest.

In particular, the adapter plane described below overcomes the technical problems known in the prior art by avoiding any mechanical uncoupling of the surgical instrument holders or of the thigh rest from the main portion of the adapter plane, from the surgical table and from the limb positioning device.

This is possible thanks to the particularly favourable structure that comprises a quick coupling device that is easily accessed by a surgeon and preferably configured to enable the positioning and coupling of the surgical instruments, even without direct contact, thus overcoming the known problems associated with the presence of the drape.

Furthermore, the presence of support portions capable of supporting both of the patient's legs makes the operations simpler and safer and provides ease of handling hitherto unknown in the prior art.

Lastly, the advantageous bilateral configuration of the present invention overcomes the inconvenience of having to use mechanical means to adjust the configuration of the adapter plane according to surgical needs.

It will thus be apparent to the expert in the field that the present invention overcomes technical problems found in the prior art which, despite continuous innovation, were hitherto unsolved, and guarantees immediate and significant advantages.

The present invention will now be described with reference to the accompanying drawings, provided purely by way of non-limiting illustration, in which.

Figure 1:
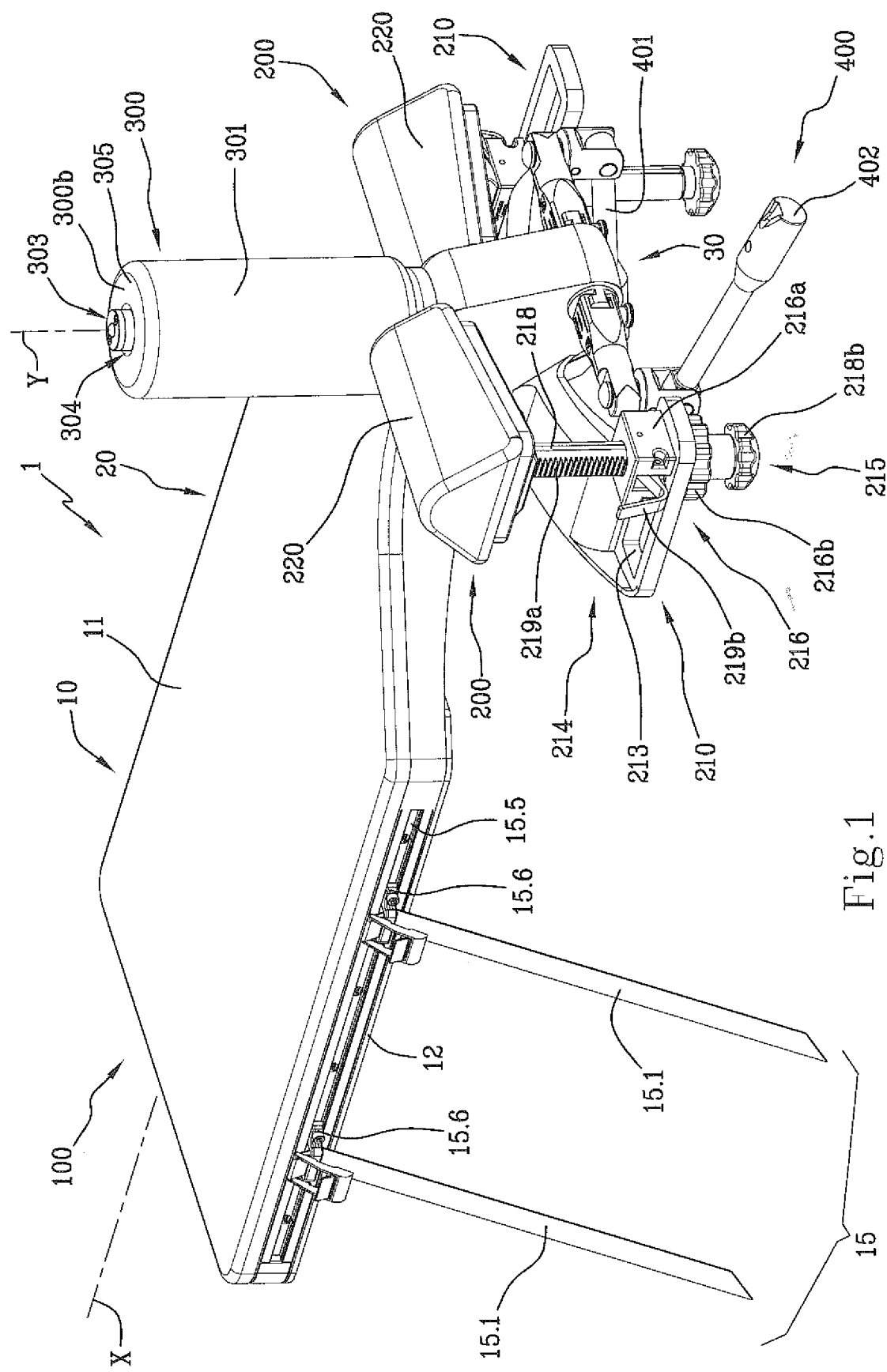
FIG. 1 is a perspective view of an adapter plane for a surgical table according to the present invention.
Figure 2:
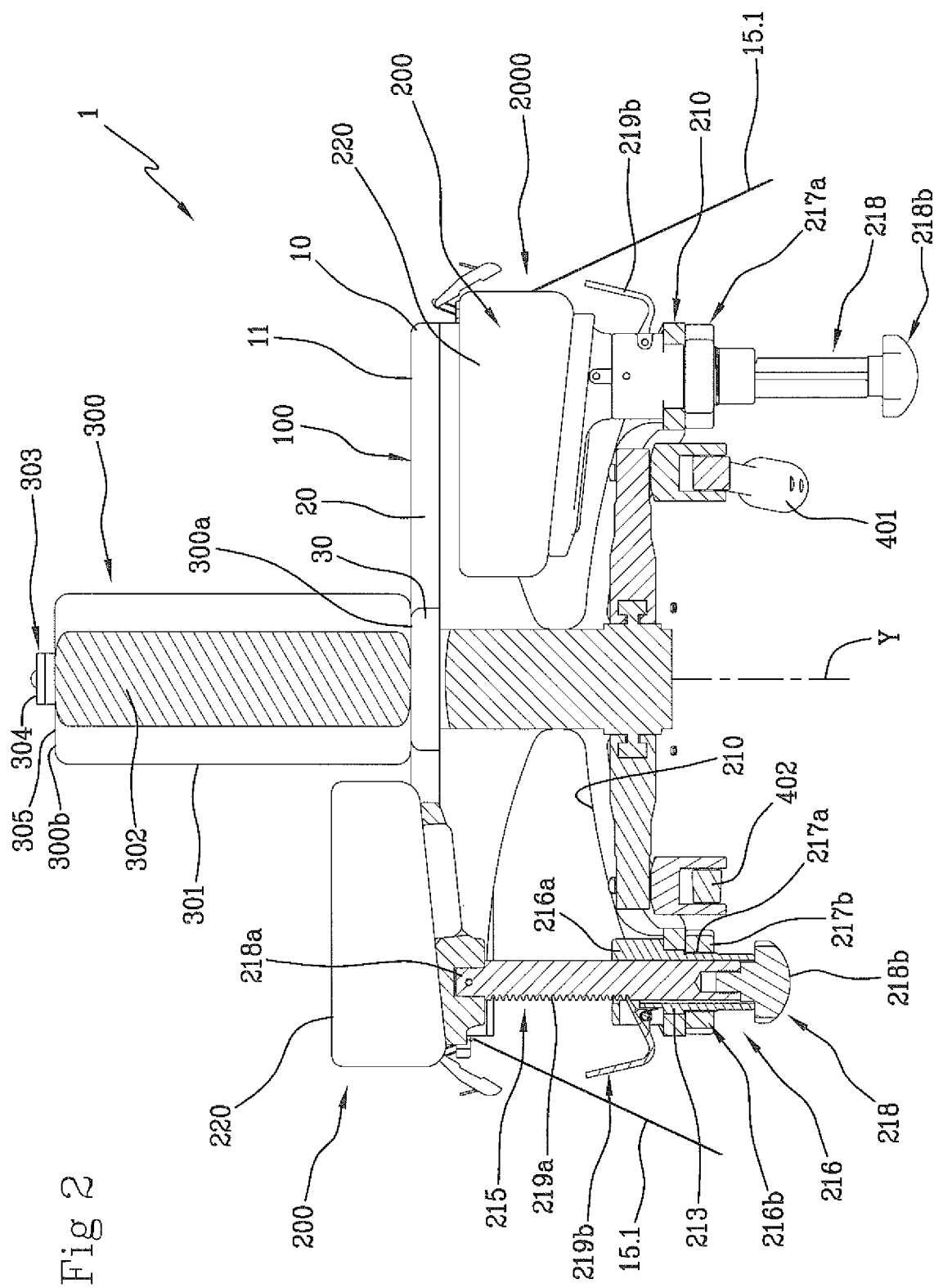
FIG. 2 is a partially sectioned view of the adapter plane of FIG. 1.

In the drawing, reference numeral 1 indicates an adapter plane for a surgical table according to the present invention.

The adapter plane for surgical table has a main body 100, with a central axis of symmetry X, a thigh rest device 2000 and a perineal support 300.

Preferably, the thigh rest device 2000 comprises two thigh rests 200 arranged laterally with respect to said central axis X, one on each side.

The main body 100 has three portions: a first portion, referred to as the proximal portion 10, substantially rectangular in shape, suitable to be placed, at least partially, on top of a conventional surgical table; a second portion, referred to as the median portion 20, formed integrally with the proximal portion 10 and trapezoidal in shape (preferably an isosceles trapezoid); a third portion, referred to as the distal portion 30, formed integrally with the median portion 20 and having a tapered shape (in particular an upturned "U" shape). Said three proximal 10, median 20 and distal 30 portions have a uniform structure and are, preferably, made of the same material. In this way, said portions 10, 20 and 30 form a unicum comprising two superimposed layers: an upper layer 11 to accommodate the patient, and a lower layer 12 comprising the structure that supports the adapter plane. The upper layer 11 may be made of a comfortable material to accommodate the patient, such as, for instance, polyethylene foam, imitation leather or the like, paying particular attention to the radiotransparency of the chosen material; the lower layer is made of ratiotransparent material such as, for instance, carbon.

Laterally with respect to the lower layer and integrally attached thereto are fixing means 15 for anchoring the adapter plane to the surgical table. A possible embodiment of said fixing means 15 is illustrated in FIG. 1. It shows two lateral rails 15.5, (only one of said two rails is illustrated in FIG. 1), coupled to each of which are a pair of sliding slides 15.6 bearing retaining means 15.6, for example belts 15.1, so as to enable quick coupling to the surgical table. Instead of the belts 15.2, the adapter plane can be equipped with rigid bars to be inserted into specific fixing means provided on the surgical table.

Preferably, the perineal support 300 is arranged on the distal portion 30 of the central body and rises from the plane from a connection end 300a to a free end 300b.

In particular, the perineal support 300 has a prismatic shape extending between two planar faces 305 respectively defining the connection end 300a and the free end 300b.

More precisely, said support 300 has a cylindrical shape with the longitudinal axis Y orthogonal with respect to the central axis X and extends axially projecting with respect to the upper layer 11. The perineal support 300 has a peripheral area 301 suitable to come into contact with the patient's body and an internal area having a tubular core 302.

Also at the distal end 30 of the central body 100, preferably coupled to the upper layer 11, the central body 100 is provided with a quick coupling device 303 for coupling the adapter plane 1 to one or more surgical instruments.

In particular, the quick coupling device 303 is configured to permit a coupling with no direct contact to said one or more surgical instruments.

In the preferred embodiment, said quick coupling device 303 is connected to the free end 300b of the perineal support 300.

Advantageously, in this way the surgical instruments are arranged in the area immediately adjacent to the hip to be operated on, directly above the patient and offer no lateral obstruction to the surgeon.

Preferably, the quick coupling device 303 comprises a magnet or electromagnet 304 that can be magnetically coupled to said one or more surgical instruments.

More precisely, the magnet or electromagnet 304 is preferably connected to the free end 300b of the perineal support 300.

The magnet or electromagnet 304 is preferably located in correspondence with a centre of the planar face 305 defining the free end 300b, so as to provide both an easily accessible coupling point and a stabilising plane that is large enough to guarantee safe coupling.

Thus, advantageously, the quick coupling device 303, preferably of the contactless type, located beneath the sterile drapes, is able to couple with additional surgical devices arranged above the sterile drapes, such as, for example, a digital device, a fluoroscopic grid, or other similar devices, without coming into contact with such equipment.

Integrally anchored to the distal portion 30 of the central body 100 is at least one support 210 placed laterally with respect to the central axis X.

Said support 210 is suitable to couplingly receive a thigh rest 200, as described more fully below.

Preferably, there are two supports 210, one on each side of the distal portion 30, which project away from one another, each suitable to couplingly receive a respective thigh rest 200. It is worth noting that, although the drawing shows a configuration in which the pair of supports 210 are arranged symmetrically with respect to the central axis X, it will be apparent to the expert in the field that this arrangement does not affect the functioning of the aforesaid supports 210.

Although this is a preferred embodiment, it should not be deemed exclusive, as the spirit of the present invention includes both the embodiment with the single thigh rest and that with the bilateral thigh rests.

That stated, hereinafter, for the sake of simplicity but without any loss of generality, specific reference will be made to the embodiment that is illustrated, provided with both supports 210, without prejudice to the fact that any characteristics applicable to the single support 210 and to the single thigh rest 200 are to be deemed applicable to the embodiment with a single thigh rest and to that with the bilateral thigh rests.

The pair of supports 210 are substantially the shape of an "L" on its side, having the longer side coupled to the lower layer 12 of the distal portion 30 of the central body 100 and the shorter side centrally hollow to form a slideway 213 in order to accommodate and guide the translation of a respective thigh rest 200. By means of the configuration described above, the longer sides of the supports 210 are substantially perpendicular to the central axis X, whereas the shorter sides of said supports 210 are parallel to the central axis X. Said pair of supports 210 are made of radiotransparent material, for example carbon. The shorter side, as already mentioned, has a central cavity that extends for a substantial part of its length, to form a slideway 213, for example a guiding eyelet.

Preferably, each lateral support 210 comprises a respective adjustment assembly 214 for adjusting the position of the thigh rest 200.

In particular, the adjustment assembly 214 comprises a vertical translation mechanism 215 and/or a horizontal translation mechanism 216 to control the vertical translation and/or horizontal translation of the respective thigh rest 200.

It is worth noting that the terms "horizontal" and "vertical" are used here to roughly characterise the movements, which are not necessarily perfectly aligned with such directions, but at least follow such directions with respect to the central axis X (i.e. horizontal) and the Y axis (i.e. vertical).

The horizontal translation mechanism 216 of the adjustment assembly 214 comprises a shoe 216a connected to the respective thigh rest 200 and slidingly connected to said slideway 213 so as to move in a direction at least partly aligned with the central axis X.

In particular, the shoe 216a carries the thigh rest 200.

The horizontal translation mechanism 216 further comprises a locking member 216b that can be selectively switched between a released position in which the shoe 216a is able to slide freely in the slideway 213 and a locked position in which it locks the position of the shoe 216a in the slideway 213.

Preferably, the locking member 216b is of the clamp type. In that respect, the shoe 216a comprises a threaded portion 217a to which a clamping nut 217b is coupled and which is able to abut against said slideway 213.

The vertical translation mechanism 215 instead comprises a stem 218 extending between an upper end 218a, bearing the thigh rest 200, and a lower end, preferably provided with a handle 218b.

The stem 218 is slidingly connected to the support 210 so as to move between a lowered position and a raised position.

To define the position of the stem 218, i.e., of the thigh rest 200, the vertical translation mechanism 215 comprises a locking device 219 that can be selectively switched between a released position in which the stem 218 is able to slide freely, and a locked position in which it locks the position of the stem 218.

Preferably, the locking device 219 is a ratchet or the like.

In other words, the locking device 219 comprises a rack 219a obtained in a side of said stem 218, and a pawl 219b that can be selectively coupled to said rack 219a.

Thus, the perimeter of the stem 218 is provided with recesses of an appropriate shape and size to couple with the pawl.

In the preferred embodiment, the pawl 219b is a lever that is elastically movable between a position in which it is engaged with the rack 219a and a disengaged position.

Preferably, the stem 218 is slidingly inserted in the shoe 216a, which is thus provided with a specific through opening to receive the stem.

The pawl 219b is thus hinged to the shoe 216a next to the opening, in order to come alongside and engage with the rack.

Said thigh rest 200 further comprises a support portion 220 against which the patient's thigh rests during the steps of the operation, and the connection portion already described.

At the distal end 30 of the central body 100, coupled to the lower layer 1, there are coupling devices 400 for one or more apparatuses for positioning the patient's limb. In the accompanying drawing, merely by way of example, two couplings 401 and 402 are illustrated, for respective apparatuses for positioning the patient's limbs.

The functioning of the adapter plane 1 according to the present invention is apparent from the description provided above and will now be briefly outlined, to enable a better understanding of the invention.

First, the adapter plane 1 is arranged over a conventional surgical table, by placing at least part of the central body 100 (preferably the proximal portion 10) on top of a conventional surgical table. The adapter plane 1 is attached to the surgical table using the fixing means 15. Two limb positioning apparatuses are then coupled to the adapter plane 1 using the coupling devices 400.

Next, the patient is placed on the surgical table, in a supine position, so that the perineal support 300 comes into contact with the patient's genital area.

In this way the patient's lumbosacral region rests on the proximal portion 10 of the central body 100 of the adapter plane 1, while the patient's legs are arranged at the sides of the perineal support 300. In particular, the lower portion of each of the patient's thighs comes into contact with a respective thigh rest 200. The position of the thigh rests 200 is adjusted, according to the size of the patient, for example according to the patient's height, by adjusting the height (by means of vertical translation parallel to the axis Y of the perineal support 300) and the position with respect to the perineal support 300 (by means of horizontal translation parallel to the central axis X). The height is adjusted by the user (for example, by the surgeon) using the stem 218 and pressing the handle 218b to raise the support portion 220 of the thigh rest 200 or pulling said handle 218b to lower said support portion 220 of the thigh rest 200.

Alternative embodiments may envisage the use of pneumatically or electrically powered actuators or other similar actuators to adjust the position of the thigh rests 200.

The patient's feet are then fastened to the limb positioning devices.

During hip replacement surgical procedures, the patient's leg is moved using limb positioning devices, according to the teachings of conventional surgical techniques. In particular, in order to operate in the region proximal to the thigh bone, the patient's leg is placed in a so-called hyperextended position, that is to say, the patient's foot is drawn towards the floor. During this hyperextension of the patient's leg, the presence of the thigh rest 200 prevents the proximal portion of the thigh bone from following its natural movement, acting as a fulcrum and creating a lever effect which causes said proximal part of the thigh bone to rotate. This rotation of the thigh bone about the thigh rest 200 exposes the proximal part of the thigh bone, through the minimally invasive incision, so that it can be seen by the surgeon.

Advantageously, this gives better access to the patient's thigh bone, while keeping the incision as small as possible.

The importance of a precise adjustment of the thigh rests 200 in order to obtain the best exposure of the proximal portion of the patient's thigh bone is therefore clear.

As is well-known to the expert in the field, the patient's left limb and right limb may differ in size. Advantageously, the present invention provides an adapter plane 1 provided with means for adjusting the thigh rests 200 separately, in order to place each limb in the correct position.

The invention claimed is:

1. An adapter plane for a surgical table, said adapter plane comprising a central body which can be coupled to a surgical table and having a proximal portion suitable to at least partially accommodate the lumbar region of a patient's body and a distal portion suitable to at least partially accommodate the sacral region of the body of a patient, said adapter plane being attachable to a surgical table by placing the central body at least partially on top of said surgical table and characterised in that, said central body comprises a perineal support having a connection end and a free end, the connection end and the free end being opposite and spaced apart from each other along an axis, the connection end of the perineal support being arranged on the distal portion of the central body, and a quick coupling device for coupling the adapter plane to one or more surgical instruments is connected to the free end of the perineal support, wherein the perineal support rises up from the adapter plane from the connection end to the free end.

2. The adapter plane as claimed in claim 1, characterised in that said quick coupling device is configured to permit a coupling without direct contact to said one or more surgical instruments.

3. The adapter plane as claimed in claim 2, characterised in that said quick coupling device comprises a magnet or electromagnet that can be magnetically coupled to said one or more surgical instruments.

4. The adapter plane as claimed in claim 1, characterised in that the perineal support is disposed in a median area of the distal portion.

5. The adapter plane as claimed in claim 4, characterised in that said perineal support comprises a magnet or electromagnet connected to said free end and at least partially defining said quick coupling device.

6. The adapter plane as claimed in claim 5, characterised in that said perineal support comprises a prismatic body extending between two planar faces respectively defining the connection end and the free end, said magnet or electromagnet being placed in correspondence with a center of the planar face defining the free end.

7. The adapter plane as claimed in claim 1, characterised in that, a thigh rest device is provided in the distal portion of the central body.

8. The adapter plane as claimed in claim 7, characterised in that said thigh rest device comprises two thigh rests, each of which is arranged on a respective side of the distal portion and is connected to said distal portion so as to each have at least one degree of freedom.

9. The adapter plane for a surgical table as claimed in claim 8 characterised in that the thigh rests are coupled to the central body by means of lateral supports comprising a slideway to enable the translation of the thigh rests.

10. The adapter plane for a surgical table as claimed in claim 9, characterised in that the lateral supports comprise a respective adjustment assembly, for adjusting the position of the thigh rests.

11. The adapter plane for a surgical table as claimed in claim 10, characterised in that the adjustment assembly comprises a vertical translation mechanism and/or a horizontal translation mechanism to control the vertical translation and/or horizontal translation of the respective thigh rest.

12. The adapter plane for a surgical table as claimed in claim 11, characterised in that said horizontal translation mechanism of the adjustment assembly comprises:
a shoe connected to the respective thigh rest and slidingly connected to said slideway;
a locking member that can be selectively switched between a released position in which the shoe is able to slide freely in the slideway and a locked position in which the locking member locks the position of the shoe in the slideway.

13. The adapter plane as claimed in claim 12, characterised in that said shoe comprises a threaded portion and said locking member comprises a clamping nut coupled to said threaded portion and able to abut against said slideway.

14. The adapter plane as claimed in claim 11, characterised in that said vertical translation mechanism comprises:
a stem extending between an upper end, bearing one of said thigh rests, and a lower end, and slidingly connected to one of said lateral supports so as to move between a lowered position and a raised position;
a locking device that can be selectively switched between a released position in which the stem is able to slide freely and a locked position in which the locking device locks the position of the stem.

15. The adapter plane as claimed in claim 14, characterised in that said locking device comprises a rack obtained in a side of said stem, and a pawl that can be selectively coupled to said rack.

16. The adapter plane for a surgical table as claimed in claim 1 characterised in that the adapter plane is made, at least partially, of radiotransparent material.

17. A surgical table characterised in that the surgical table comprises an adapter plane as claimed in claim 1.

* * * * *